US009795757B2

(12) United States Patent
Miller

(10) Patent No.: US 9,795,757 B2
(45) Date of Patent: Oct. 24, 2017

(54) FLUID INLET ADAPTER

(71) Applicant: CareFusion 303, Inc., San Diego, CA (US)

(72) Inventor: Jeffrey Harold Miller, Irvine, CA (US)

(73) Assignee: VYAIRE MEDICAL CAPITAL LLC, Yorba Linda, CA (US)

( * ) Notice: Subject to any disclaimer, the term of this patent is extended or adjusted under 35 U.S.C. 154(b) by 264 days.

(21) Appl. No.: 13/931,496

(22) Filed: Jun. 28, 2013

(65) Prior Publication Data
US 2015/0000653 A1   Jan. 1, 2015

(51) Int. Cl.
*A62B 9/02* (2006.01)
*A61M 16/08* (2006.01)
(Continued)

(52) U.S. Cl.
CPC ...... *A61M 16/0816* (2013.01); *A61M 39/223* (2013.01); *F16L 19/005* (2013.01);
(Continued)

(58) Field of Classification Search
CPC ...... A61M 16/0816; A61M 2039/1077; A61M 39/223; A61M 16/08; A61M 39/10; A61M 2039/1005; A61M 2039/1044; A61M 2039/105; A61M 2039/1066; F16L 37/56; F16L 55/1018; Y10T 137/598;
(Continued)

(56) References Cited

U.S. PATENT DOCUMENTS 2,037,880 A   4/1936   Charavay
2,510,125 A   6/1950   Meakin
(Continued)

FOREIGN PATENT DOCUMENTS

CN   1041204 A   4/1990
CN   101225881 A   7/2008
(Continued)

OTHER PUBLICATIONS

Invitation to Pay Additional Fees in International Application No. PCT/US2014/044737 dated Oct. 28, 2014, 7 pages.
(Continued)

*Primary Examiner* — Todd J Scherbel
*Assistant Examiner* — Victoria Leszczak
(74) *Attorney, Agent, or Firm* — McDermott Will & Emery LLP

(57) ABSTRACT

An adapter for selectively providing fluid to a device from one of multiple fluid sources has a body with a first inlet for connecting a first one of the multiple fluid sources to the device and a second inlet for connecting a second one of the multiple fluid sources to the device. The adapter also includes a handle that is movably coupled to the body and includes an access control element. The handle is configured to secure the body to a device when the adapter is in either of a first position or a second position that is rotated relative to the first configuration. The access control element obstructs access to the second inlet when the adapter is secured to the device in the first position and the access control element obstructs access to the first inlet when the adapter is secured to the device in the second position.

19 Claims, 7 Drawing Sheets

(51) Int. Cl.
*F16L 19/00* (2006.01)
*A61M 39/22* (2006.01)
*F16L 37/113* (2006.01)
*F16L 37/56* (2006.01)
*A61M 39/10* (2006.01)

(52) U.S. Cl.
CPC . *A61M 39/1011* (2013.01); *A61M 2039/1005* (2013.01); *A61M 2039/1077* (2013.01); *A61M 2039/1083* (2013.01); *A61M 2202/0208* (2013.01); *A61M 2205/14* (2013.01); *F16L 37/113* (2013.01); *F16L 37/56* (2013.01); *Y10T 137/598* (2015.04)

(58) Field of Classification Search
CPC ... Y10T 137/0447; A61G 12/005; E04H 3/08; F24F 7/00
USPC ........ 137/270, 269; 285/136.1, 141.1, 142.1, 285/124.2, 124.4, 45
See application file for complete search history.

(56) References Cited

U.S. PATENT DOCUMENTS

| | | | |
|---|---|---|---|
| 2,634,311 | A | 4/1953 | Darling |
| 3,140,042 | A | 7/1964 | Fujii |
| 3,673,541 | A | 6/1972 | Volinskie |
| 3,776,215 | A * | 12/1973 | Howard .................. F24F 6/14 126/113 |
| 3,788,765 | A | 1/1974 | Rusak |
| 4,167,369 | A | 9/1979 | Ishihara |
| 4,243,357 | A | 1/1981 | Flynn et al. |
| 4,381,668 | A | 5/1983 | Sato et al. |
| 4,543,041 | A | 9/1985 | French et al. |
| 4,562,744 | A | 1/1986 | Hall et al. |
| 4,571,801 | A | 2/1986 | Ewing |
| 4,649,760 | A | 3/1987 | Wedding |
| 4,754,651 | A | 7/1988 | Shortridge et al. |
| 4,763,645 | A | 8/1988 | Kapp |
| 4,809,742 | A | 3/1989 | Grau |
| 4,825,904 | A | 5/1989 | Grau et al. |
| 4,909,545 | A | 3/1990 | Hohol |
| 4,978,281 | A | 12/1990 | Conger, IV |
| 5,064,346 | A | 11/1991 | Atarashi et al. |
| 5,127,400 | A | 7/1992 | DeVries et al. |
| 5,190,068 | A | 3/1993 | Philbin |
| 5,265,594 | A | 11/1993 | Olsson et al. |
| 5,277,196 | A | 1/1994 | Hankinson et al. |
| 5,295,397 | A | 3/1994 | Hall et al. |
| 5,331,995 | A | 7/1994 | Westfall et al. |
| 5,339,807 | A | 8/1994 | Carter |
| 5,365,795 | A | 11/1994 | Brower, Jr. |
| 5,461,932 | A | 10/1995 | Hall et al. |
| 5,478,206 | A | 12/1995 | Prahst |
| 5,537,992 | A | 7/1996 | Bjoernstijerna et al. |
| 5,572,992 | A | 11/1996 | Kankkunen et al. |
| 5,604,681 | A | 2/1997 | Koeninger |
| 5,606,236 | A | 2/1997 | Tennies et al. |
| 5,771,884 | A | 6/1998 | Yarnall et al. |
| 5,918,596 | A | 7/1999 | Heinonen |
| 5,954,051 | A | 9/1999 | Heinonen et al. |
| 6,017,315 | A | 1/2000 | Starr et al. |
| 6,139,262 | A | 10/2000 | Ravidranath |
| 6,151,557 | A | 11/2000 | Broden et al. |
| 6,422,092 | B1 | 7/2002 | Morrison et al. |
| 6,422,256 | B1 | 7/2002 | Balazy et al. |
| 6,553,923 | B2 | 4/2003 | Gatley, Jr. |
| 6,578,818 | B1 | 6/2003 | Krimmer et al. |
| 6,609,431 | B1 | 8/2003 | Tietsworth et al. |
| 6,622,724 | B1 | 9/2003 | Truitt et al. |
| 6,820,620 | B2 | 11/2004 | Rochat |
| 6,945,123 | B1 | 9/2005 | Kuehl et al. |
| 7,107,834 | B2 | 9/2006 | Meneghini et al. |
| 7,121,139 | B2 | 10/2006 | Shajii et al. |
| 7,636,640 | B2 | 12/2009 | Wang et al. |
| 7,819,022 | B2 | 10/2010 | Hope |
| 7,826,986 | B2 | 11/2010 | McDonald |
| 8,504,318 | B2 | 8/2013 | Mendelson et al. |
| 9,003,877 | B2 | 4/2015 | Qasimi et al. |
| 2002/0085952 | A1 | 7/2002 | Ellingboe et al. |
| 2002/0198668 | A1 | 12/2002 | Lull et al. |
| 2003/0106554 | A1 | 6/2003 | de Silva et al. |
| 2003/0220605 | A1 | 11/2003 | Bowman et al. |
| 2004/0074311 | A1 | 4/2004 | Lull et al. |
| 2004/0177703 | A1 | 9/2004 | Schumacher et al. |
| 2004/0187871 | A1 | 9/2004 | Kimmel et al. |
| 2005/0004534 | A1 * | 1/2005 | Lockwood .......... A61M 1/0031 604/304 |
| 2005/0241412 | A1 | 11/2005 | Tison et al. |
| 2006/0076419 | A1 | 4/2006 | Johnson |
| 2006/0079765 | A1 | 4/2006 | Neer et al. |
| 2006/0144163 | A1 | 7/2006 | Friberg |
| 2006/0162466 | A1 | 7/2006 | Wargo et al. |
| 2006/0236781 | A1 | 10/2006 | Ohmi et al. |
| 2007/0193369 | A1 | 8/2007 | Evans et al. |
| 2007/0265877 | A1 | 11/2007 | Rice et al. |
| 2007/0277824 | A1 * | 12/2007 | Aylsworth ........ A61M 16/0666 128/204.23 |
| 2008/0059084 | A1 | 3/2008 | Wang et al. |
| 2008/0092891 | A1 | 4/2008 | Cewers |
| 2008/0105259 | A1 | 5/2008 | de Silva et al. |
| 2008/0283062 | A1 | 11/2008 | Esposito, Jr. |
| 2009/0038615 | A1 | 2/2009 | Bradley |
| 2009/0093774 | A1 | 4/2009 | Wang et al. |
| 2009/0095068 | A1 | 4/2009 | Redemann et al. |
| 2009/0113996 | A1 | 5/2009 | Wang et al. |
| 2009/0293634 | A1 | 12/2009 | Ong |
| 2009/0326839 | A1 | 12/2009 | Rogers et al. |
| 2010/0031737 | A1 | 2/2010 | Saito et al. |
| 2010/0139660 | A1 | 6/2010 | Adahan |
| 2010/0229967 | A1 | 9/2010 | Yasuda et al. |
| 2010/0236552 | A1 | 9/2010 | Kwok et al. |
| 2010/0307490 | A1 | 12/2010 | Broborg et al. |
| 2011/0100364 | A1 | 5/2011 | Faram |
| 2011/0126834 | A1 | 6/2011 | Winter et al. |
| 2011/0126837 | A1 | 6/2011 | Winter et al. |
| 2011/0301867 | A1 | 12/2011 | Davis et al. |
| 2012/0065533 | A1 | 3/2012 | Carrillo, Jr. et al. |
| 2012/0085349 | A1 | 4/2012 | Tobias et al. |
| 2012/0185102 | A1 | 7/2012 | Skoglund et al. |
| 2012/0204874 | A1 | 8/2012 | Sofranko |
| 2012/0226449 | A1 | 9/2012 | Delache et al. |
| 2012/0229272 | A1 | 9/2012 | Jacob et al. |
| 2012/0284991 | A1 | 11/2012 | Kusz et al. |
| 2012/0285454 | A1 | 11/2012 | Nibu et al. |
| 2012/0285455 | A1 | 11/2012 | Varga et al. |
| 2012/0318383 | A1 | 12/2012 | Yasuda et al. |
| 2013/0036806 | A1 | 2/2013 | Kohno |
| 2013/0079667 | A1 | 3/2013 | Berkcan et al. |
| 2013/0153040 | A1 | 6/2013 | Goto et al. |
| 2013/0220314 | A1 | 8/2013 | Bottom |
| 2013/0247905 | A1 | 9/2013 | Miller et al. |
| 2014/0054479 | A1 | 2/2014 | Shen |
| 2014/0066880 | A1 | 3/2014 | Prince et al. |
| 2014/0182590 | A1 | 7/2014 | Platt et al. |
| 2014/0251322 | A1 | 9/2014 | Miller |
| 2015/0020807 | A1 | 1/2015 | Kimmel |
| 2015/0096560 | A1 | 4/2015 | Klenner et al. |
| 2015/0143921 | A1 | 5/2015 | Postberg et al. |
| 2016/0256646 | A1 | 9/2016 | Vazales |

FOREIGN PATENT DOCUMENTS

| | | |
|---|---|---|
| CN | 101687086 A | 3/2010 |
| CN | 102155570 A | 8/2011 |
| CN | 202366282 U | 8/2012 |
| CN | 102686888 A | 9/2012 |
| CN | 102927292 A | 2/2013 |
| CN | 103041492 A | 4/2013 |
| CN | 202870631 U | 4/2013 |
| EP | 0829793 A1 | 3/1998 |
| EP | 1127583 A2 | 8/2001 |
| EP | 1658874 A2 | 5/2006 |

(56) References Cited

FOREIGN PATENT DOCUMENTS

| EP | 2402616 A1 | 1/2012 |
|---|---|---|
| JP | S56597 A | 1/1981 |
| WO | WO-0138832 A2 | 5/2001 |
| WO | WO-2006024532 A1 | 3/2006 |
| WO | WO-2011055254 A1 | 5/2011 |
| WO | WO-2013002699 A1 | 1/2013 |

OTHER PUBLICATIONS

International Search Report and Written Opinion for International Application No. PCT/US2014/044737, dated May 19, 2015, 18 pages.
International Search Report for International Application No. PCT/US2014/044743, dated Jan. 22, 2015, 6 pages.
International Search Report and Written Opinion in PCT Application No. PCT/US2014/044438 dated Oct. 28, 2014, 11 pages.
International Search Report and Written Opinion in PCT Application No. PCT/US2014/044441 dated Oct. 31, 2014, 12 pages.
International Search Report and Written Opinion in PCT Application No. PCT/US2014/044724 dated Oct. 21, 2014, 12 pages.
Invitation to Pay Additional Fees in PCT Application No. PCT/US2014/044743 dated Oct. 21, 2014, 7 pages.
International Search Report and Written Opinion in PCT Application No. PCT/US2014/044442 dated Nov. 3, 2014, 10 pages.
International Search Report and Written Opinion for Application No. PCT/US2015/038157, dated Nov. 5, 2015, 12 pages.
International Search Report and Written Opinion for Application No. PCT/US2015/038155, dated Dec. 17, 2015, 18 pages.
Invitation to Pay Additional Fees and Partial Search Report for Application No. PCT/US2015/038155, dated Oct. 7, 2015, 7 pages.
Chinese Office Action for Application No. 201480036606.9, dated Sep. 2, 2016, 6 pages excluding translation.
Chinese Office Action for Application No. 201480037090.X, dated Sep. 26, 2016, 6 pages excluding English translation.
Chinese Office Action for Application No. 201480036971.X, dated Oct. 8, 2016, 10 pages excluding English translation.
Chinese Office Action for Application No. 201480037104.8, dated Nov. 17, 2016, 5 pages excluding English translation.

\* cited by examiner

FLUID INLET ADAPTER

CROSS-REFERENCE TO RELATED APPLICATIONS

Not applicable.

BACKGROUND

Field

The present disclosure generally relates to fluid inlet ports and, in particular, a configurable adapter that can accept a fluid from either of two sources having different connectors.

Description of the Related Art

Patients with respiratory injury, such as chronic respiratory failure, may be provided with a respirator to assist with their breathing or, in severe cases, take over the breathing function entirely. Respirators typically provide a flow of air, or other breathing gases, at an elevated pressure during an inhalation interval, followed by an exhalation interval where the pressurized air is diverted so that the air within the patient's lungs can be naturally expelled.

Conventional respirators may be configured to accept one or more breathing gases, for example "pure oxygen" or "heliox 80/20" (a mixture of 80% helium with 20% oxygen) from external sources. It is important to configure the respirator according to the gas provided, for example connecting to a source of pure oxygen to be mixed with compressed air to provide an oxygen-enriched air to a patient as compared to connecting to a source of pure heliox that is to be provided undiluted to the patient. Conventional respirators may require manual identification of the gas being provided and carries a risk that a user may not correctly identify the gas that is actually being provided.

SUMMARY

The disclosed fluid inlet adapter provides a fluid inlet that can be configured to accept only one of two possible fluids at a time and provide a machine-readable indication as to which fluid is currently being accepted.

In certain embodiments, an adapter for selectively providing fluid to a device from one of multiple fluid sources is disclosed. The adapter includes a body, a first inlet for connecting a first one of the multiple fluid sources to the device, and a second inlet for connecting a second one of the multiple fluid sources to the device. Each of the first and second inlets are coupled to the body. The adapter also includes a handle movably coupled to the body and comprising an access control element. The handle is configured to secure the body to a device when the adapter is in either of a first position or a second position that is rotated 180° relative to the first configuration. The access control element obstructs access to the second inlet when the adapter is secured to the device in the first position and the access control element obstructs access to the first inlet when the adapter is secured to the device in the second position.

In certain embodiments, a ventilator is disclosed that has a housing comprising a fluid passage and an adapter that includes a body, a first inlet for connecting a first one of the multiple fluid sources to the device, and a second inlet for connecting a second one of the multiple fluid sources to the device. Each of the first and second inlets are coupled to the body. The adapter also includes a handle movably coupled to the body and comprising an access control element. The handle is configured to secure the body to a device when the adapter is in either of a first position or a second position that is rotated 180° relative to the first configuration. The access control element obstructs access to the second inlet when the adapter is secured to the device in the first position and the access control element obstructs access to the first inlet when the adapter is secured to the device in the second position.

In certain embodiments, a method is disclosed that includes the step of orienting an adapter relative to a housing of a ventilator in either a first configuration when it is desired to configure the ventilator to accept a first gas mixture in a second configuration that is rotated 180° relative to the first configuration when it is desired to configure the ventilator to accept a second gas mixture. The method also includes the step of engaging the adapter with a docking location of the ventilator such that a first inlet is in fluid communication with a fluid passage of the housing when the adapter is oriented in the first configuration and a second inlet is in fluid communication with the fluid passage of the housing when the adapter is oriented in the second configuration. The method also includes the step of activating a handle to secure the adapter to the housing, wherein the handle comprises an access control element that obstructs access to the second inlet when the adapter is secured to the housing in the first configuration and obstructs access to the first inlet when the adapter is secured to the housing in the second configuration. The method also includes the step of sensing automatically with a sensor of the ventilator the location of a machine-detectable indicator that is disposed in a first location relative to the housing when the adapter is secured to the housing in the first configuration and disposed in a second location that is different from the first location when the adapter is secured to the housing in the second configuration.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

It is advantageous to provide a fluid inlet that can be configured to accept only one of two possible fluids at a time and provide a machine-readable indication as to which fluid is currently being accepted.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar.

While the discussion herein is directed to the provision of oxygen and heliox to a ventilator in healthcare environment, application of the methods and concepts disclosed here in not limited to this application or field. It will be apparent to those of skill in the art that the inlet adapter may be utilized in other fields and applications that use multiple types of fluids as inputs, for example chemical processing.

Figure 1:
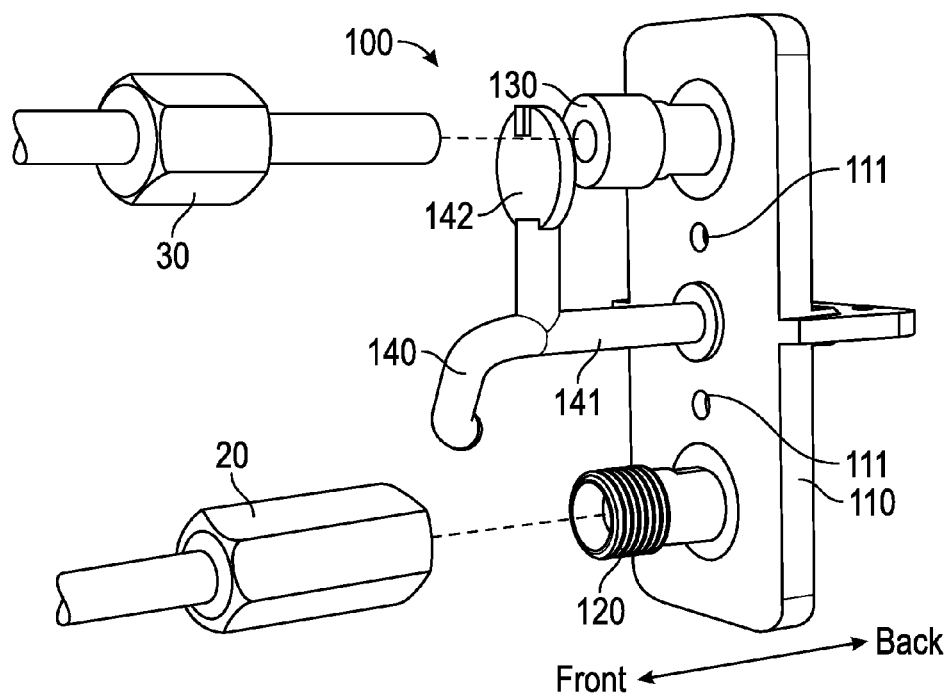
FIGS. 1-2 are front and back perspective views of an exemplary fluid inlet adapter according to certain aspects of the present disclosure.
Figure 2:
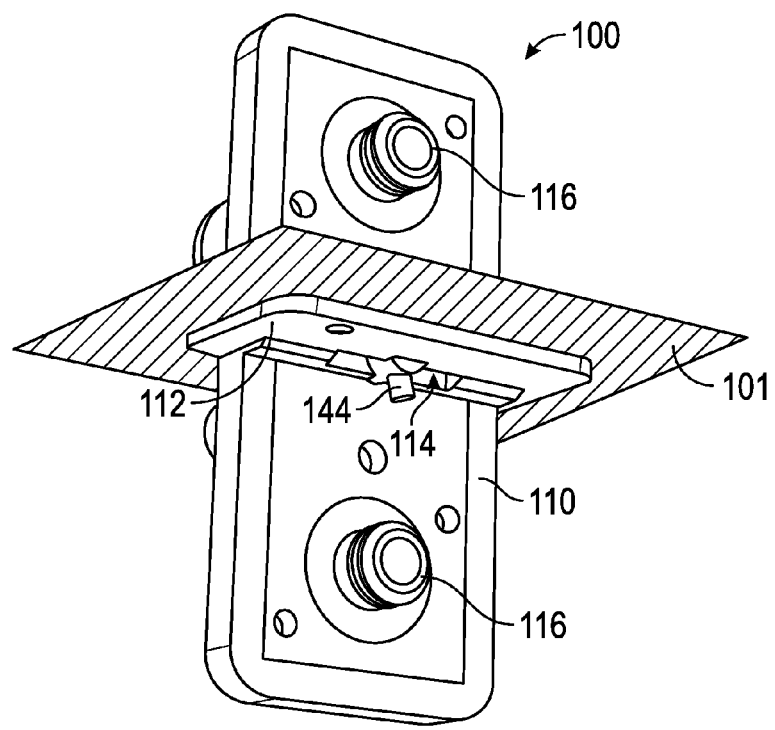

FIGS. 1-2 are front and back perspective views of an exemplary fluid inlet adapter 100 according to certain aspects of the present disclosure. In FIG. 1, the fluid inlet adapter 100, also referred to herein as "the adapter 100," comprises a body 110 with two inlets 120, 130 that are configured to respectively mate with connectors 20, 30 that are connected to two different fluid sources. In certain embodiments, the two connectors 20 and 30 may comprise different configurations comprising attributes such as shape, the presence or absence of thread, keys, etc. Example connector configurations are shown in FIGS. 7-10. A handle 140 is movably coupled to the body 110 and comprising an access control element 142. In certain embodiments, the access control element 142 is a paddle extending from a shaft 141 that is, in this example, perpendicular to the body 110. The handle 140 is shown in FIG. 1 in a latched position, wherein the access control element 142 is positioned in front of inlet 130, thereby preventing a user from connecting a connector 30 to the inlet 130. In certain embodiments, the access control element 142 is disposed in front of the inlet 130. In certain embodiments, the access control element 142 is disposed proximate to the inlet 130, e.g. adjacent to the side of the inlet 130, so as to interfere with the attachment of a connector 30 to the inlet 130 and substantially prevents connection to the inlet 130 when the adapter 100 is in the position shown in FIG. 1. The inlet 120 is fully accessible in this position of the adapter 100 and a user may connect a connector 20 to the inlet 120. The body 110 may include one or more keying holes 111 that engage pins, posts, or other keying features (not shown in FIG. 1A) of the connectors 20, 30.

FIG. 2 depicts the back of the adapter 100. A center plane 101 is defined relative to the body 110 and bisects the body 110. There is an alignment feature 112 extending from the body 110 that is centered on the center plane 101. There are two ports 116 that are identical in form that are coupled to the body 110 and symmetrically disposed on opposite sides of the center plane 101. The adapter 100 has a first position, as shown in FIG. 2, and a second position that is rotated 180° from the first position with respect to the plane of symmetry. Positions of the adapter 100 are discussed in greater detail with respect to FIGS. 5 and 6. The adapter 100 also comprises first and second coupling ports 116 that are symmetrically located on opposite sides of the center plane 101 on a back side of the body 110. The first and second coupling ports 116 are in respective fluid communication with the first and second inlets 120, 130. In certain embodiments, the coupling ports 116 may be respectively aligned with the first and second inlets 120, 130. In certain embodiments, the coupling ports 116 may be respectively offset from the first and second inlets 120, 130.

It can be seen in FIG. 2 that the handle 140 comprises a latching pin 144 that is disposed within a securing feature, for example slot 114 formed in the alignment feature 112. The latching pin 144, in this example, extends outward from the portion of the shaft 141 that extends beyond the bottom of the body 110. The function of the pin latching 144 and the method by which the handle 140 secures the adapter 100 to a device, for example a ventilator (not shown), is discussed in greater detail with respect to FIGS. 4A-4B.

Figure 3A:
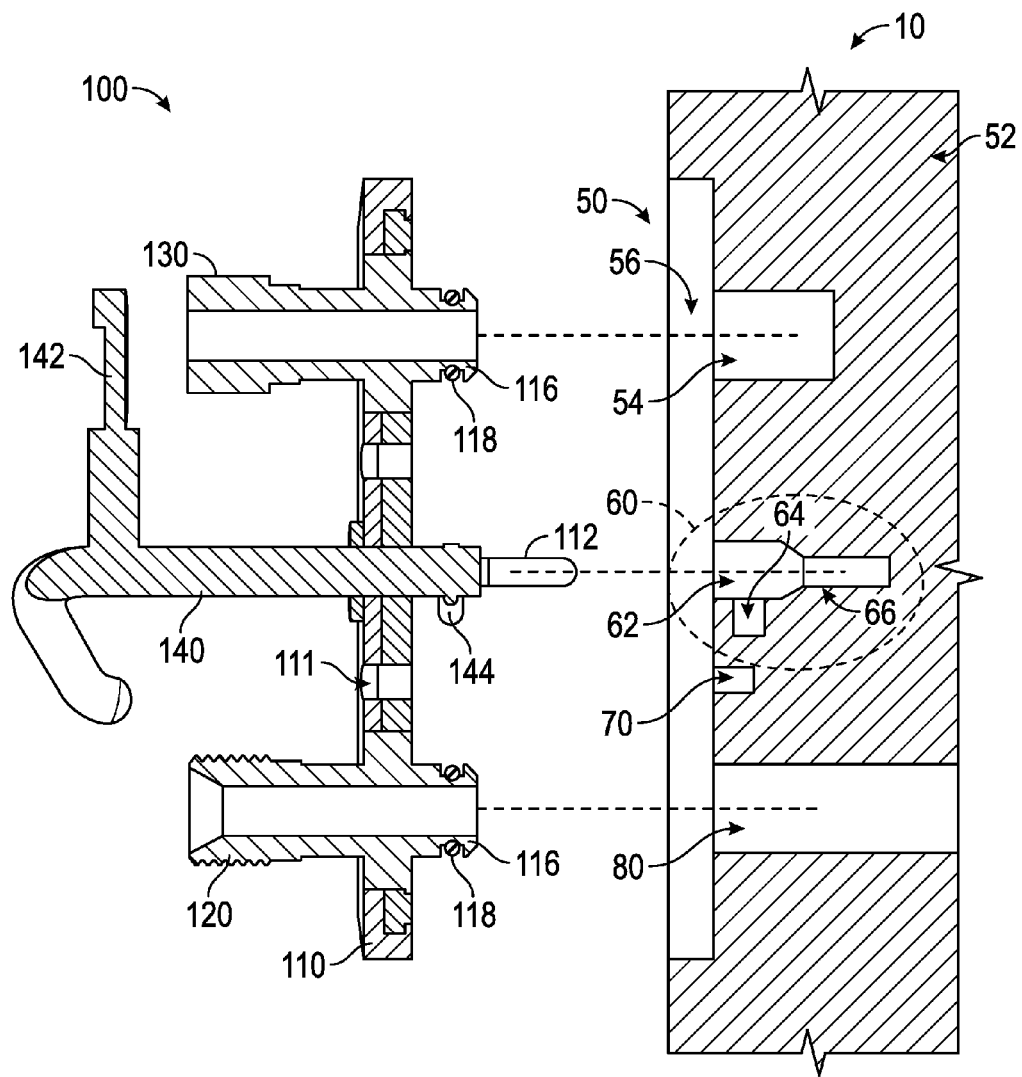
FIG. 3A is a cross-sectional side view of an exemplary fluid inlet adapter and a device according to certain aspects of the present disclosure.

FIG. 3A is a cross-sectional side view of the exemplary fluid inlet adapter 100 and a device 10 according to certain aspects of the present disclosure. The device 10 has a housing 52 with, in this example, a docking station 50 having an alignment slot 66 that is configured to accept the alignment feature 112. In this example, there is a recess 62 adjacent to the alignment slot 66 that is configured to accept an end of the handle 140. A latching slot 64 extends laterally from the recess 62 and is configured to engage the pin 144 when the handle 140 is rotated such that the pin extends from the alignment feature 112, as is discussed in greater detail with respect to FIGS. 4A-4B.

The housing 52 comprises a fluid passage 80 is configured to accept a flow of a fluid. In certain embodiments, the device 10 is a ventilator and the fluid passage 80 connects to a blower (not shown) that pumps the fluid from fluid passage 80 to a patient as is generally known to those of skill in the art and not repeated herein. The fluid passage 80 is positioned relative to the alignment slot 66 such that one of the coupling ports 116 will be at least partially disposed within the fluid passage 80 when the adapter 100 is secured to the device 10 in either a first or second position. FIG. 3A depicts the example adapter 100 secured to the docking station 50 in the first position, wherein the coupling port 116 that is in fluid communication with inlet 120 is also at least partially disposed within and in fluid communication with the fluid passage 80. In the second position (not shown in FIG. 3A), the adapter 100 is upside down from the position shown in FIG. 3A such that the coupling port 116 that is in fluid communication with inlet 130 is also at least partially disposed within and in fluid communication with the fluid passage 80. In certain embodiments, the coupling ports 116 may have a sealing feature 118, for example an o-ring, that are configured to detachably and sealingly mate with the fluid passage 80. The housing also comprises a blind recess 54 that accepts the un-used coupling port 116. The docking location 50 may have a recess 56 configured to accept the body 110 such that the front of the body 110 is flush with the surface of the housing 52. In certain embodiments, the docking location 50 may also have a recess 70 position under a keying hole 111. The recess 70 may provide clearance for a keying feature of a mating connector or may provide a retention function.

Figure 3B:
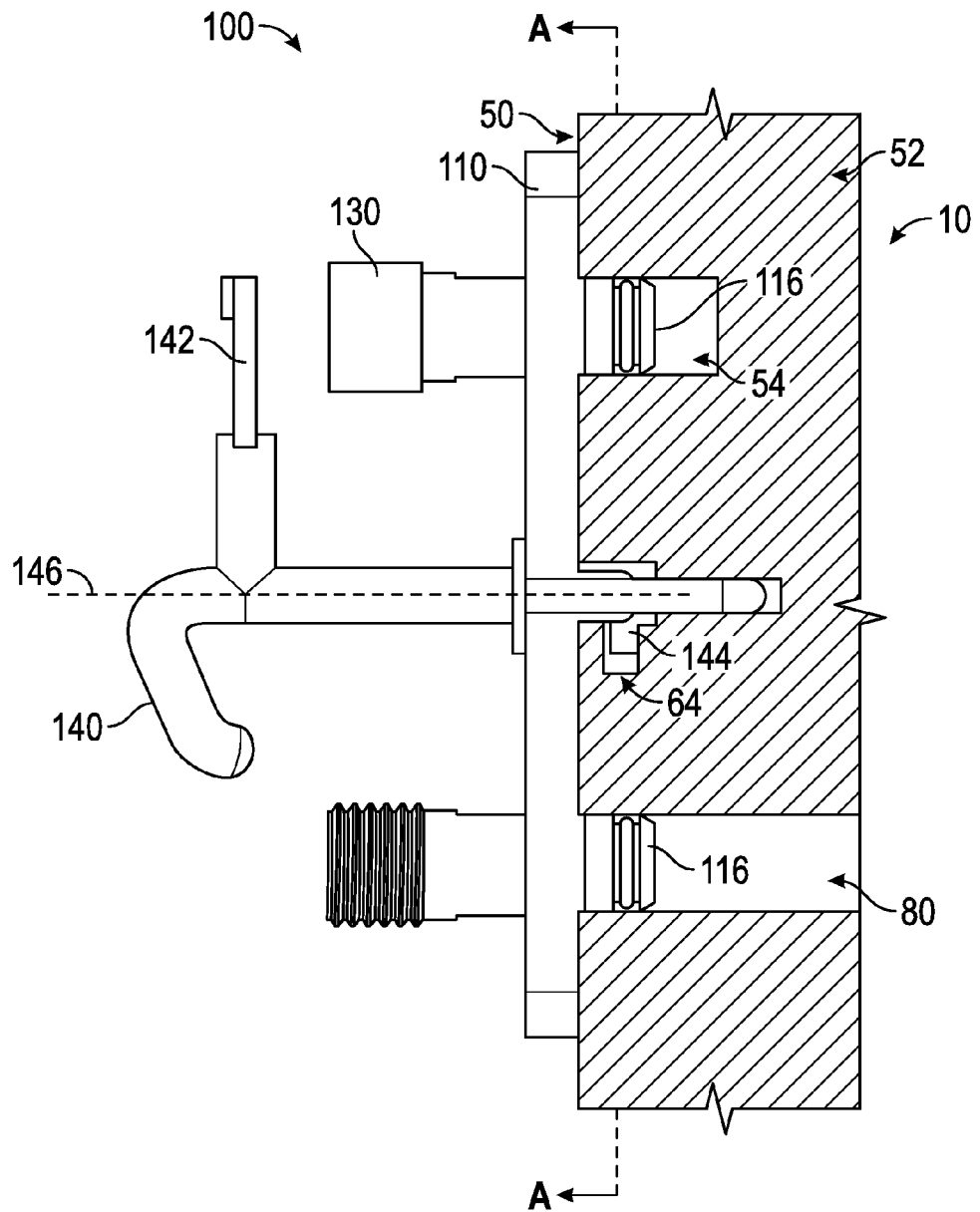
FIG. 3B is a cross-sectional side view of the exemplary fluid inlet adapter of FIG. 3A mated with the docking location of the housing according to certain aspects of the present disclosure.

FIG. 3B is a cross-sectional side view of the exemplary adapter 100 of FIG. 3A mated with the docking location 50 of the housing 52 according to certain aspects of the present disclosure. It can be seen that the lower coupling port 116 is partially disposed within the fluid passage 80 and the upper coupling port 116 is partially disposed within the blind recess 54.

Figure 4A:
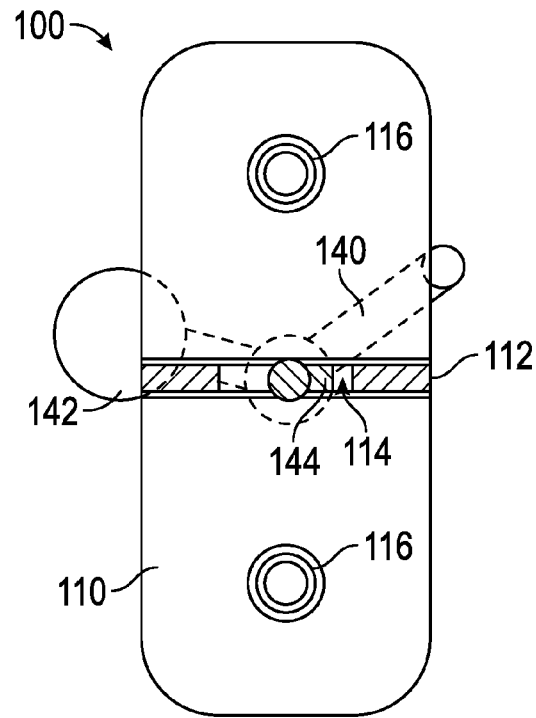
FIGS. 4A-4B depict the position of the handle in exemplary unlatched and latched positions according to certain aspects of the present disclosure.
Figure 4B:
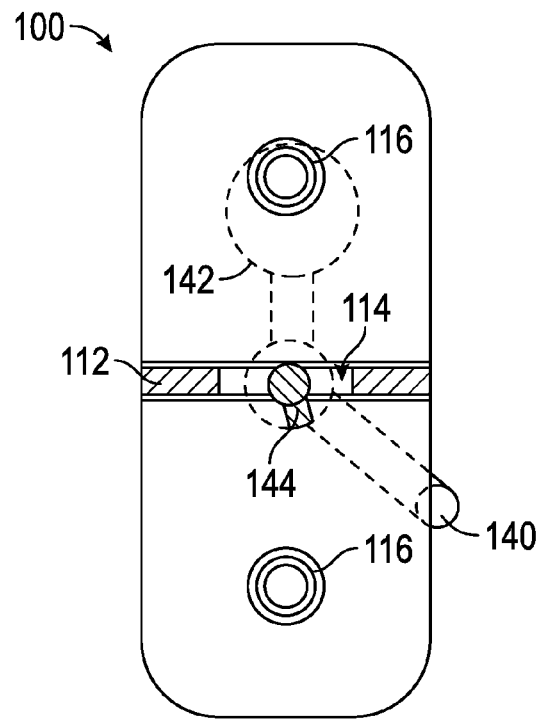

FIGS. 4A-4B depict the position of the handle 140 in exemplary unlatched and latched positions according to certain aspects of the present disclosure. FIG. 4A depicts the position of the handle 140 while in a "unlatched" position suitable for insertion of the alignment feature 112 into the alignment slot 66 of the docking station 50. The pin 144 is positioned completely within the slot 114 so as not to interfere with the alignment slot 66. Once the adapter 100 is fully seated in the docking station 50, the handle 140 can be turned to the position shown in FIG. 4B.

FIG. 4B depicts a "latched" position with handle 140 rotated so as to engage pin 144 in latching slot 64. In this position of handle 140, the access control element 142 is disposed in front of the inlet 130 thereby obstructing access to the inlet 130 so as to discourage connection of a connector 30 to the inlet 130 while the adapter 100 is secured to the device 10 in this position.

Figure 5:
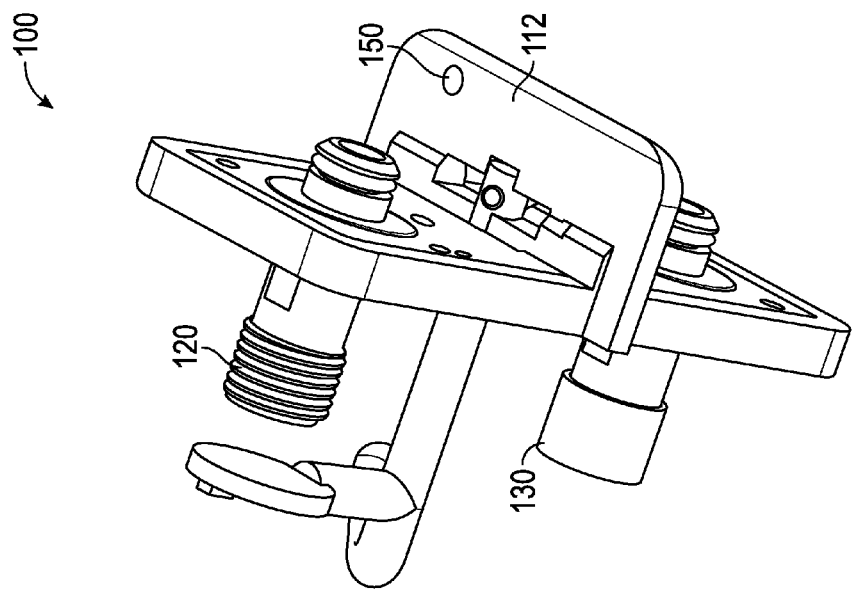
FIGS. 5 and 6 depict an exemplary inlet adapter configured to accept fluid from two different sources according to certain aspects of the present disclosure.
Figure 6:
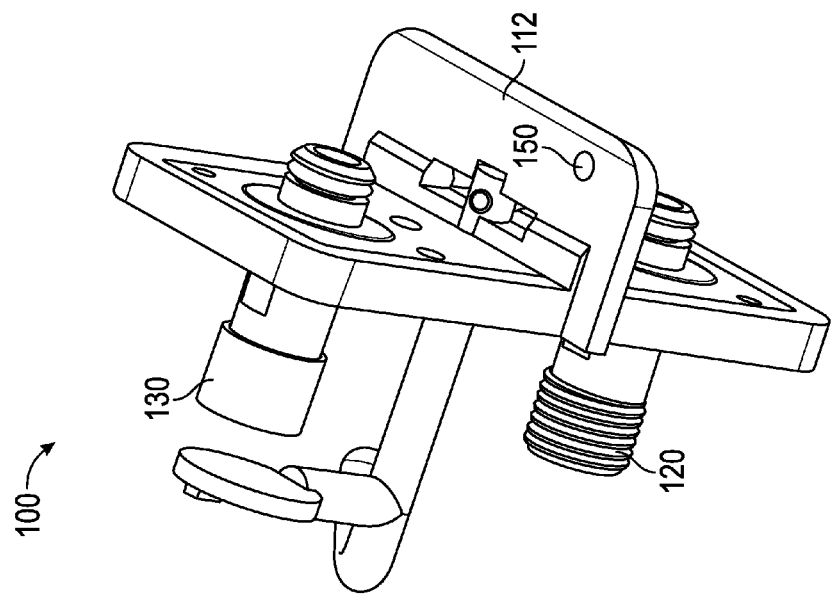

FIGS. 5 and 6 depict an exemplary inlet adapter 100 configured to accept fluid from two different sources 20, 30 according to certain aspects of the present disclosure. FIG. 5 depicts the adapter 100 configured to enable inlet 120 to allow a connector 20 (not shown in FIG. 5) while blocking connection to the inlet 130. It can be seen that the machine-detectable indicator 150 is positioned in a first position, e.g. on the near side of alignment feature 112.

FIG. 6 depicts the adapter 100 reversed in orientation and configured to allow inlet 130 to accept a connector 30 (not shown in FIG. 6) while blocking connection to the inlet 120. It can be seen that when the adapter 100 is disposed in this position, which is the reverse of the position of FIG. 5, that the machine-detectable indicator 150 is positioned in a second position, e.g. on the far side of alignment feature 112, that is also the reverse of FIG. 5.

With respect to the positions of the machine-detectable indicators 150 in FIGS. 5 and 6, the device 50 may have a first sensor (not shown in FIG. 5) positioned so as to detect the presence of the sensor in the position of FIG. 5 and a second sensor positioned so as to detect the presence of the sensor in the position of FIG. 6. The use of two sensors may provide a positive indication of the position of the adapter 100 and, therefore, a positive indication of which gas is being provided.

Figure 7:
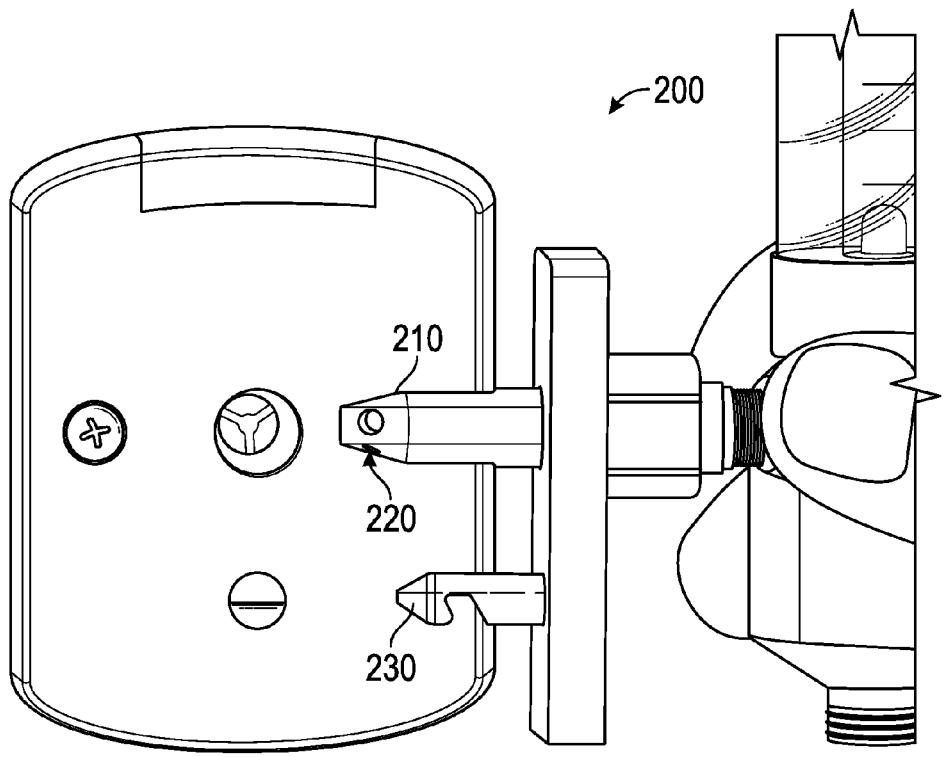
FIGS. 7-10 depict example connector configurations according to certain aspects of the present disclosure.

FIGS. 7-10 depict example connector configurations according to certain aspects of the present disclosure. The adapter 100 may comprise inlets that are configured to accept one of these type of connectors. FIG. 7 depicts an "Ohmeda style" gas connection 200 wherein the gas-specific configuration of the connector is accomplished by one or more notches 220 on the outlet face 210 and a pin 230 on the adaptor. The notches 220 and pins 230 may vary in position and/or size based on the gas required.

Figure 8:
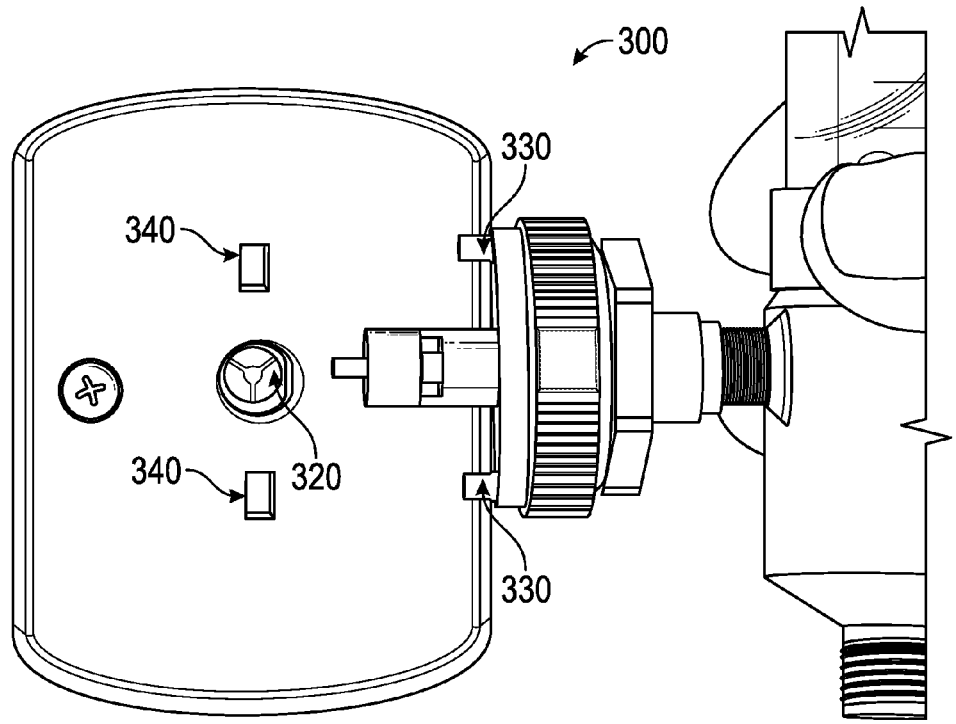

FIG. 8 depicts a "Chemetron style" gas connection 300 wherein the gas-specific configuration of the connector is accomplished by the position and shape of the latching hole 320 on the outlet face and alignment tabs 330 that mate with recesses 340. The latching hole 320 will vary in position and shape based on the gas required.

Figure 9:
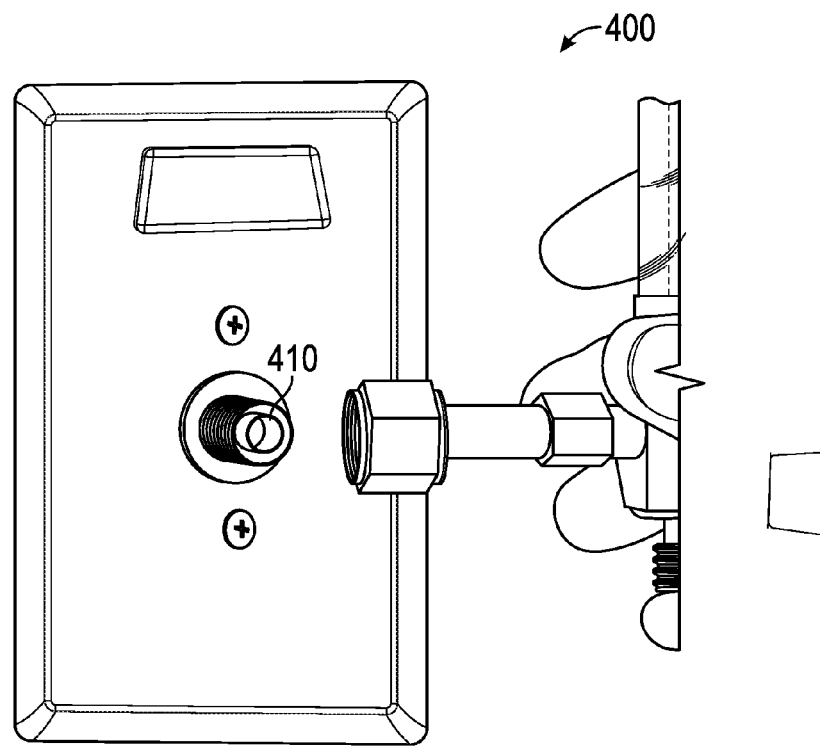

FIG. 9 depicts a "Diameter Index Safety System (DISS) style" gas connection 400 wherein the gas-specific configuration of the connector is accomplished by gas-specific threads disposed on a barrel 410. The thread diameter and adaptor nipple size may vary based on the gas required.

Figure 10:
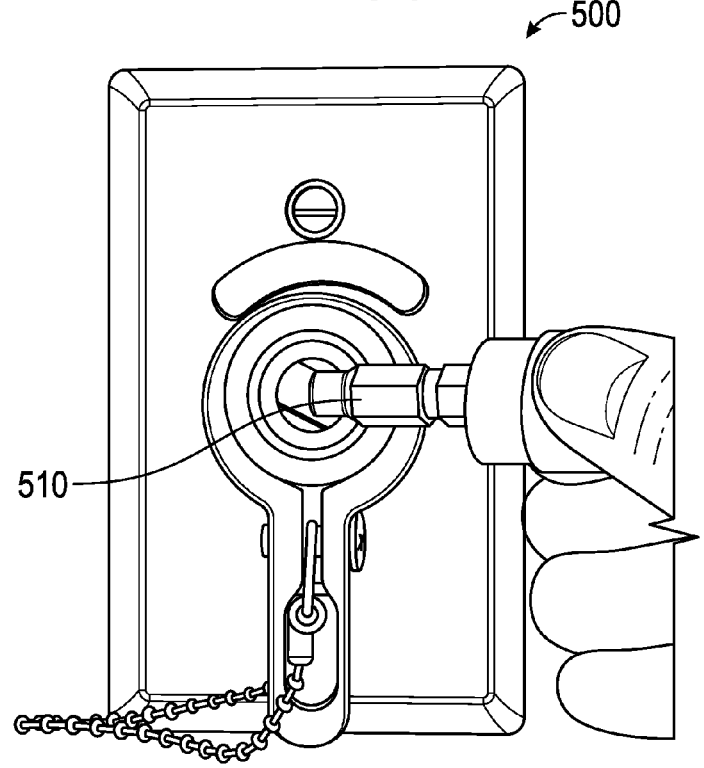

FIG. 10 depicts a "Schrader style" gas connection 500 wherein the gas-specific configuration of the connector is accomplished by geometric indexing, i.e. each gas has a unique shape and size of the barrel 510

It can be seen that the disclosed embodiments of the inlet adapter provide a reliable means of configuring a device, such as a ventilator, to accept only one of a possible variety of gases. While the disclosed embodiment of the adapter has two inlets and accepts gas through one inlet while blocking the other inlet, other embodiments of the adapter may have three or more inlets and may be configured to accept gas through more than one of the three or more inlets. In addition, the machine-detectable indicator that is disclosed as a magnet herein may be any machine-readable element, for example a barcode or 2D matrix positioned to be read by a camera or scanner when the adapter is configured in a certain position.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. To the extent that the terms "include," "have," or the like are used in the description or the claims, such terms are intended to be inclusive in a manner similar to the term "comprise" as "comprise" is interpreted when employed as a transitional word in a claim. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

Nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

All structural and functional equivalents to the elements of the various aspects described throughout this disclosure that are known or later come to be known to those of ordinary skill in the art are expressly incorporated herein by reference and are intended to be encompassed by the claims.

What is claimed is:

1. An adapter for selectively providing fluid to a device from one of multiple fluid sources, the adapter comprising:
   a body;
   a first inlet for connecting a first one of the multiple fluid sources to the device and a second inlet for connecting a second one of the multiple fluid sources to the device, each of the first and second inlets coupled to the body; and
   a handle that is movably coupled to the body and comprises an access control element and a shaft, the shaft integrally formed with the handle, the shaft being rotationally coupled to the body and the shaft being configured for detachably coupling the body to the device to secure the body to the device when the adapter is in either of a first position or a second position that is rotated 180° relative to the first position, wherein when the adapter is secured to the device in the first position a first empty space is between the access control element and the second inlet and the access control element is adjacent to the second inlet to obstruct access to the second inlet and when the adapter is secured to the device in the second position a second empty space is between the access control element and the first inlet and the access control element is adjacent to the first inlet to obstruct access to the first inlet.

2. The adapter of claim 1, wherein the first inlet is configured to mate with a first connector that is connected to the first one of the multiple fluid sources and the second inlet is configured to mate with a second connector that is connected to the second one of the multiple fluid sources.

3. The adapter of claim 2, wherein the second connector is a different type of connector from the first connector.

4. The adapter of claim 2, wherein:
   the first connector is associated with a first gas mixture; and
   the second connector is associated with a second gas mixture that is different from the first gas mixture.

5. The adapter of claim 1, wherein:
   the body comprises a center plane; and
   the first and second inlets are symmetrically located on opposite sides of the center plane.

6. The adapter of claim 5, further comprising first and second coupling ports that are symmetrically located on opposite sides of the center plane on a back side of the body, the first and second coupling ports being in respective fluid communication with the first and second inlets.

7. The adapter of claim 6, wherein the first and second coupling ports are identical and located such that the first coupling port is partially disposed within a fluid passage of the device when the adapter is secured to the device in the first position and the second coupling port is partially disposed within the fluid passage of the device when the adapter is secured to the device in the second position.

8. The adapter of claim 7, wherein the first and second coupling ports are each configured to detachably and sealingly mate with the fluid passage of the device.

9. The adapter of claim 1, wherein the handle further comprises a latching pin configured to engage a securing feature of the device so as to secure the adapter to the device in either of the first and second positions.

10. The adapter of claim 1, wherein the access control element comprises a paddle that is disposed proximate to the second inlet when the adapter is secured to the device in the first position and disposed proximate to the first inlet when the adapter is secured to the device in the second position.

11. The adapter of claim 1, further comprising a machine-detectable indicator that is disposed in a first location relative to the device when the adapter is secured to the device in the first position and disposed in a second location that is different from the first location when the adapter is secured to the device in the second position.

12. A ventilator comprising:
    a housing comprising a fluid passage; and
    an adapter comprising:
       a body;
       a first inlet and a second inlet each coupled to the body; and
       a handle that is movably coupled to the body and comprising an access control element and a shaft, the shaft integrally formed with the handle, the shaft being rotationally coupled to the body and the shaft being configured for detachably coupling the body to the housing to secure the body to the housing in either of a first position or a second position that is rotated 180° relative to the first position, wherein when the adapter is secured to the housing in the first position a first empty space is between the access control element and the second inlet and the access control element is adjacent to the second inlet to obstruct access to the second inlet and when the adapter is secured to the housing in the second position a second empty space is between the access control element and the first inlet and the access control element is adjacent to the first inlet to obstruct access to the first inlet.

13. The ventilator of claim 12, wherein the first inlet is configured to mate with a first connector and the second inlet is configured to mate with a second connector.

14. The ventilator of claim 13, wherein the second connector is a different connector type from the first connector.

15. The ventilator of claim 13, wherein:
    the first connector is associated with a first gas mixture; and
    the second connector is associated with a second gas mixture that is different from the first gas mixture.

16. The ventilator of claim 12, wherein:
    the body comprises a center plane; and
    the first and second inlets are symmetrically located on opposite sides of the center plane.

17. The ventilator of claim 16, wherein:
    the housing further comprises a docking location configured to accept the adapter in either of the first or second positions, the docking location comprising a fluid passage;
    the adapter further comprises a first coupling port and a second coupling port that are symmetrically located on opposite sides of the center plane on a back side of the body such that the first coupling port is partially disposed within the fluid passage when the adapter is secured to the docking location in the first position and the second coupling port is partially disposed within the fluid passage when the adapter is secured to the docking location in the second position, the first and second coupling ports being in respective fluid communication with the first and second inlets.

18. The ventilator of claim 17, wherein the first and second coupling ports are each configured to detachably and sealingly mate with the fluid passage of the housing.

19. The ventilator of claim 17, wherein:
the housing further comprises a securing feature; and
the handle further comprises a latching pin configured to engage the securing feature of the housing when the adapter is secured to the docking location in either of the first and second positions and the handle is in a latched position,
wherein the latching pin is disengaged from the securing feature when the handle is in an unlatched position.

* * * * *